United States Patent [19]
Suzuki et al.

[11] Patent Number: 5,508,063
[45] Date of Patent: Apr. 16, 1996

[54] TANTALUM COMPOUND, PROCESS OF PRODUCING THE SAME, AND MATERIAL FOR FORMING TANTALUM OXIDE FILMS

[75] Inventors: Toshiyuki Suzuki, Toda; Hideyuki Mori; Kouichi Nakamura, both of Urawa, all of Japan

[73] Assignee: Japan Energy Corporation, Tokyo, Japan

[21] Appl. No.: 346,009

[22] Filed: Nov. 29, 1994

[30] Foreign Application Priority Data

Dec. 2, 1993 [JP] Japan ................................ 5-302755

[51] Int. Cl.$^6$ ........................ C23C 16/00; C07F 9/00
[52] U.S. Cl. ...................... 427/255.3; 427/248.1; 556/42; 556/43
[58] Field of Search ............... 556/42, 43; 427/248.1, 427/255.3

[56] References Cited

PUBLICATIONS

Chamberlain et al., Organometallics, vol. 1, No. 8, pp. 1098–1100 (1982).
R. N. Kapoor, et al., Indian J. Chem., vol. 5, pp. 442–443 (1967).
D. C. Bradley, et al., J. Chem. Soc., pp. 726–728 (1955).
Thomas Kauffmann, et al., Tetrahedron Letters, vol. 23, No. 22, pp. 2301–2304 (1982).

*Primary Examiner*—Porfirio Nazario-Gonzales
*Attorney, Agent, or Firm*—Flynn, Thiel, Boutell & Tanis

[57] ABSTRACT

A novel tantalum compound represented by the formula (1): $Ta(CH_3)_3(OR)_2$, wherein R is an alkyl group having from 2 to 7 carbon atoms. The novel tantalum compound is produced by reacting a haloalkoxytantalum compound represented by the formula (2): $TaX_n(OR)_{5-n}$, wherein X is halogen, R is an alkyl group having from 2 to 7 carbon atoms, and n is an integer of from 0 to 4, with a methylmetal compound; and recovering the tantalum compound represented by the above formula (1) by reduced pressure distillation. The tantalum compound has a high vapor pressure and permits effective formation of a uniform film of tantalum oxide with good properties by a CVD method. Therefore, the tantalum compound is very useful for manufacturing semiconductor devices.

2 Claims, 1 Drawing Sheet

TANTALUM COMPOUND, PROCESS OF PRODUCING THE SAME, AND MATERIAL FOR FORMING TANTALUM OXIDE FILMS

BACKGROUND OF THE INVENTION

1. Field of the Invention

The present invention relates to a novel tantalum compound, a method of producing the compound, and a material comprising the compound as an effective component for forming tantalum oxide films.

This tantalum compound is useful for forming an insulating film having a high dielectric constant (hereinafter, referred to as a high dielectric insulating film) in a form of tantalum oxide during a process of manufacturing semiconductor devices.

2. Description of the Prior Art

Tantalum oxide films are the focus of interests and attention as a high dielectric insulating film used for manufacturing semiconductor devices such as very-large-scale integrated (VLSI) memories such as dynamic random-access memories (DRAMs) with a storage capacity of 64 M or larger per chip.

The tantalum film of the type described may be formed by means of chemical vapor deposition (CVD) in which alkoxytantalum such as pentaethoxytantalum is decomposed thermally and a decomposition product thereof is deposited on a substrate.

However, in order to uniformly feed pentaethoxytantalum to a CVD device, the feeding should be carried out at an elevated temperature or at a higher degree of depressurization due to the low vapor pressure of pentaethoxytantalum and undesirable troubles, such as deterioration of components of a feeding system due to such a high temperature feeding, may arise.

SUMMARY OF THE INVENTION

The present invention is directed to overcome the above mentioned problem and an object thereof is to provide a novel tantalum compound having a high vapor pressure which can be dealt with easily, a method of producing the compound, and a material comprising it as an effective component for forming tantalum oxide films.

The present inventor had made tremendous studies to achieve the above mentioned object and found a set of novel tantalum compounds that are useful as materials for forming tantalum oxide films. The present invention was thus reached on the basis of such finding.

More specifically, the present invention is a novel tantalum compound represented by the following formula (1):

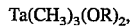

$$Ta(CH_3)_3(OR)_2,$$

wherein R is an alkyl group having from 2 to 7 carbon atoms.

The present invention also relates to a method of producing the tantalum compound represented by the above formula (1), the method comprising: reacting a haloalkoxytantalum compound represented by the following formula (2):

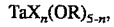

$$TaX_n(OR)_{5-n},$$

wherein X is halogen, R is an alkyl group having from 2 to 7 carbon atoms, and n is an integer of from 0 to 4, with a methylmetal compound; and recovering the tantalum compound represented by the formula (1) by means of reduced pressure distillation.

In addition, the present invention is directed to a material for forming a tantalum oxide film, the material comprising, as an effective component, the tantalum compound represented by the above formula (1).

DETAILED DESCRIPTION OF THE PREFERRED EMBODIMENTS

Particularly preferable examples of the tantalum compound represented by the formula (1) according to the present invention include trimethyldiethoxytantalum [Ta(CH$_3$)$_3$(OC$_2$H$_5$)$_2$], trimethyldiisopropoxytantalum [Ta(CH$_3$)$_3$(OCH(CH$_3$)$_2$)$_2$], and trimethyl-di-sec-butoxytantalum [Ta(CH$_3$)$_3$(OCH(CH$_3$)C$_2$H$_5$)$_2$]. With an alkyl group having only one carbon atom, the resultant compound becomes unstable and is thus involved in some troubles in handling. On the other hand, when the number of carbons of the alkyl group exceeds 7, the vapor pressure unfavorably reduces to significantly lower than that of pentaethoxytantalum.

The above mentioned trimethyldiethoxytantalum [Ta(CH$_3$)$_3$(OC$_2$H$_5$)$_2$] is a colorless transparent oily compound at a low temperature of around 40° C. However, it turns to a light-yellow transparent compound at a room temperature, and is decomposed immediately while generating heat and fume when exposed to the air. Boiling points of this compound are 30° C., 60° C., and 80° C. at absolute pressures of 1.6 Torr, 6.0 Torr, and 12.0 Torr, respectively. It decomposes at 131° C. $^1$H-NMR and $^{13}$C-NMR spectra thereof are as follows:

$^1$H-NMR (in C$_6$D$_6$, TMS, δ ppm): 0.34 (9H, s), 1.28 (6H, t, J=6.9 Hz), 4.46 (4H, q, J=6.9 Hz), and $^{13}$C-NMR (in C$_6$D$_6$, TMS, proton noise decoupling, δ ppm): 19.0, 50.6, 67.7.

The above mentioned trimethyldiisopropoxytantalum [Ta(CH$_3$)$_3$(OCH(CH$_3$)$_2$)$_2$] is a colorless transparent liquid, and is decomposed immediately while generating heat and fume when exposed to the air. Boiling points of this compound are 45° C., and 49° C. at absolute pressures of 0.7 Torr, and 1.1 Torr, respectively. $^1$H-NMR and $^{13}$C-NMR spectra thereof are as follows:

$^1$H-NMR (in C$_6$D$_6$, TMS, δ ppm): 0.41 (9H, s), 1.36 (12H, d, J=6.0 Hz), 4.83 (2H, m) and $^{13}$C-NMR (in C$_6$D$_6$, TMS, proton noise decoupling, δ ppm): 26.1, 50.8, 74.9.

The above mentioned trimethyl-di-sec-butoxytantalum [Ta(CH$_3$)$_3$(OCH(CH$_3$)C$_2$H$_5$)$_2$] is a colorless transparent liquid, and is decomposed in a short period while generating heat when exposed to the air. Boiling points of this compound are 58° C., and 70° C. at absolute pressures of 0.15 Torr, and 0.3 Torr, respectively. $^1$H-NMR and $^{13}$C-NMR spectra thereof are as follows:

$^1$H-NMR (in $C_6D_6$, TMS, δ ppm): 0.38 (9H, s), 0.98 (6H, t, J=7.5 Hz), 1.32 (6H, d, J=6.0 Hz), 1.67 (4H, m), 4.53 (2H, m) and $^{13}$C-NMR (in $C_6D_6$, TMS, proton noise decoupling, δ ppm): 10.6, 23.3, 32.6, 50.7, 79.6.

Figure 1:
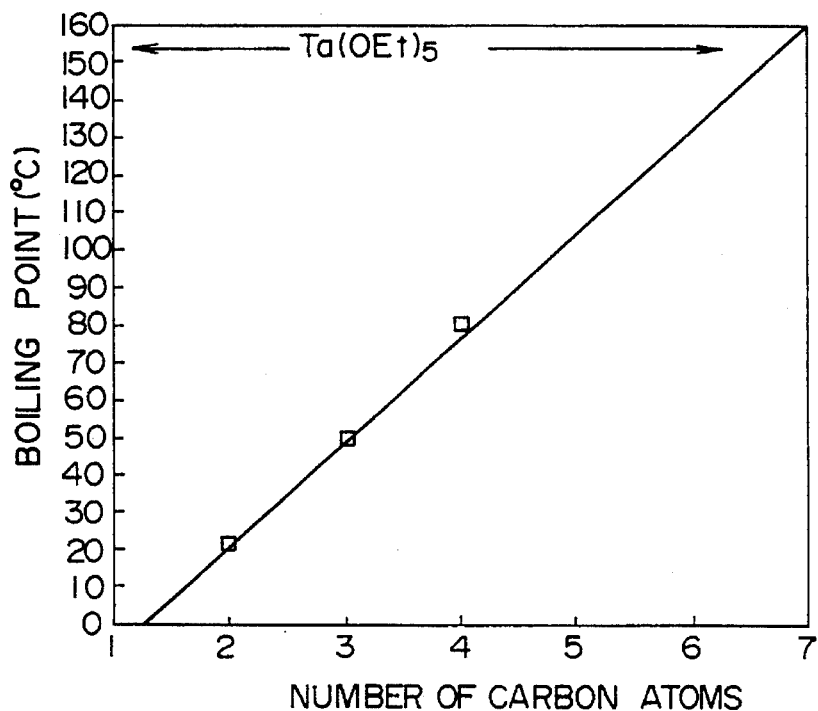
FIG. 1 is a graphical representation of boiling point (Pressure: 1 Torr) as a function of the number of carbon atoms contained in R on a tantalum compound represented by the formula (1) according to the present invention, in comparison with those of Ta(OEt)$_5$.
Figure 2:
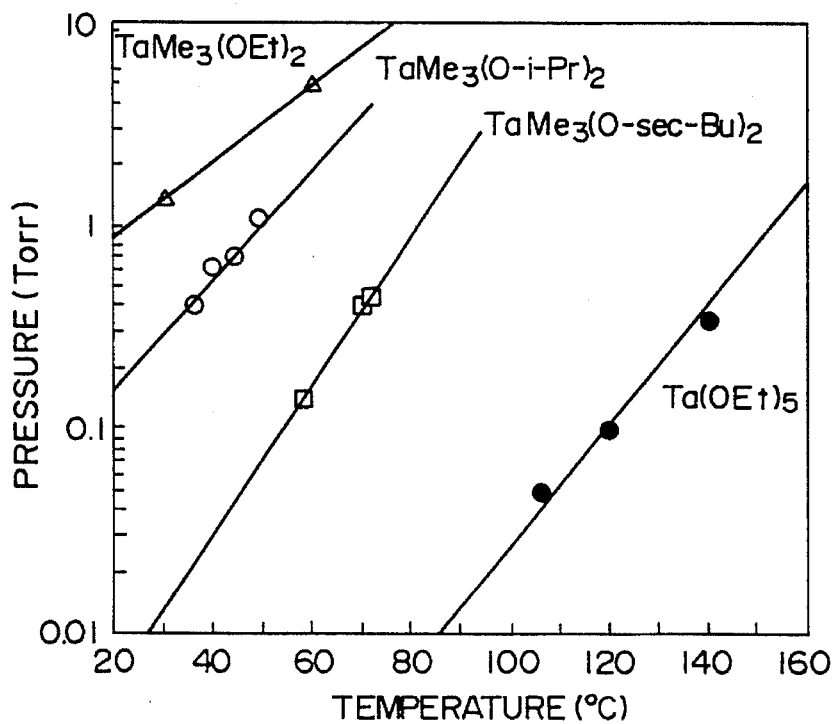
FIG. 2 is a graphical representation of vapor pressure as a function of temperature on the tantalum compounds according to the present invention, in comparison with those of Ta(OEt)$_5$.

Boiling points, and a relation between temperature and vapor pressure of these compounds are illustrated in Figs. 1 and 2, respectively, in comparison with those of $Ta(OEt)_5$.

The above mentioned tantalum compound represented by the formula (1) according to the present invention may be obtained by reacting a haloalkoxytantalum compound represented by the following formula (2) with a methylmetal compound:

$$TaX_n(OR)_{5-n},$$

wherein X is halogen such as chlorine, bromine, and iodine, and preferably chlorine; R is an alkyl group having from 2 to 7 carbon atoms, and preferably an alkyl group having from 2 to 4 carbon atoms such as ethyl, n-propyl, isopropyl, n-butyl, sec-butyl, tert-butyl, pentyl, hexyl, and heptyl; and n is from 0 to 4, and preferably from 0 to 3.

Of the tantalum compounds represented by the above formula (2), particularly preferable examples include pentaethoxytantalum, pentaisopropoxytantalum, penta-sec-butoxytantalum, dichlorotriethoxytantalum, dichlorotriisopropoxytantalum, dichloro-tri-sec-butoxytantalum, trichlorodiethoxytantalum, trichlorodiisopropoxytantalum, and trichloro-di-sec-butoxytantalum.

Of these compounds used as preferable starting materials, pentaethoxytantalum, pentaisopropoxytantalum, and penta-sec-butoxytantalum are known substances. For these compounds, commercially available ones may be used in the present invention as they are. Other starting materials such as dichlorotriethoxytantalum, dichlorotriisopropoxytantalum, and dichloro-tri-sec-butoxytantalum may be obtained by means of reaction of pentachlorotantalum with an excessive amount of ethanol, isopropyl alcohol, or sec-butyl alcohol. Alternatively, these compounds may be obtained by means of reaction of pentaethoxytantalum, pentaisopropoxytantalum, or penta-sec-butoxytantalum with chlorination agent such as acetyl chloride. In addition, trichlorodiethoxytantalum, trichlorodiisopropoxytantalum, or trichloro-di-sec-butoxytantalum may be obtained readily by means of quantitative reaction of pentachlorotantalum with ethanol, isopropyl alcohol, or sec-butyl alcohol. Alternatively, these compounds may be obtained readily by means of quantitative reaction of pentachlorotantalum with pentaethoxytantalum, pentaisopropoxytantalum, or penta-sec-butoxytantalum.

Examples of the methylmetal compound include methyllithium, Grignard's reagents such as methylmagnesium bromide, and trimethylaluminum. Of these, it is most preferable to use methyllithium in view of reaction activity.

It is preferable to conduct the reaction between the tantalum compound represented by the formula (2) and the methylmetal compound in the presence of an organic solvent such as diethyl ether, dipropyl ether, dibutyl ether, or tetrahydrofuran in order to achieve smooth reaction. In this reaction, when dichlorotriethoxytantalum, dichlorotriisopropoxytantalum, or dichloro-tri-sec-butoxytantalum is used as a starting material, it is preferable to use from 2 to 5 molar equivalent of methylmetal compound per one mole of the starting material. On the other hand, when pentaethoxytantalum, pentaisopropoxytantalum, or penta-sec-butoxytantalum is used as a starting material, it is preferable to use from 2 to 10 molar equivalent of methylmetal compound per one mole of the starting material. The reaction is conducted at between −70° C. and 0° C., and preferably at between −50° C. to −20° C. The reaction is completed in a period of from several minutes to an hour.

After completion of reaction, the solvent is removed, and the tantalum compound represented by the formula (1) of the present invention is recovered by means of reduced pressure distillation. It is preferable to conduct this distillation at 0.01–15 Torr by an absolute pressure. This is because distillation at this pressure range permits to restrict decomposition and to recover the above mentioned tantalum compound in high yield.

EXAMPLE 1

107 g of pentachlorotantalum was dispersed in 500 ml of toluene, to which 175 ml of ethanol was added dropwise in a nitrogen gas atmosphere. The resultant solution was stirred at room temperature for 1.5 hours and was then heated to 55° C. to remove the solvent by distillation. As a result, 120 g of dichlorotriethoxytantalum $[TaCl_2(OC_2H_5)_3]$ was obtained a residue in the form of white solid.

This solid was dissolved in 200 ml of diethyl ether. The mixture was cooled to −40° C., to which 1,180 ml of diethyl ether solution of methyllithium (1.1 mol/l) was added dropwise, little by little. The resultant solution was stirred at −40° C. for 1.5 hours. The solvent was then removed therefrom by distillation. Brown solid obtained as the residue was subjected to reduced pressure distillation at 80° C. and 12 Torr to obtain 44.0 g of a colorless transparent liquid. This liquid was analyzed through gas chromatography (column: Silicone OV-101, 25 m×0.25 mmφ), $^1$H-NMR, and $^{13}$C-NMR. As a result, it was found that this liquid is a sole substance. The liquid had the above mentioned physical properties and was determined as trimethyldiethoxytantalum.

EXAMPLE 2

31.1 g of pentaethoxytantalum $[Ta(OC_2H_5)_5]$ was dissolved in 100 ml of toluene, to which 10.9 ml of acetyl chloride $(CH_3COCl)$ was added dropwise in a nitrogen gas atmosphere. The resultant solution was stirred at 80° C. for 1 hour, and the solvent was then removed therefrom at 50° C. by distillation. As a result, 29.6 g of dichlorotriethoxytantalum was obtained as a residue in the form of white solid.

This solid was dissolved in 100 ml of diethyl ether. The mixture was cooled to −40° C., to which 135 ml of diethyl ether solution of methyllithium (1.1 mol/l) was added dropwise, little by little. The resultant solution was stirred at −40° C. for 1.5 hours. The solvent was then removed therefrom by distillation. Brown solid obtained as the residue was subjected to reduced pressure distillation at 40° C. and 0.2 Torr to obtain 44.0 g of a colorless transparent liquid. This liquid was analyzed in the same manner as in Example 1. The liquid had the above mentioned physical properties and was determined as trimethyldiethoxytantalum.

EXAMPLE 3

11.8 g of pentachlorotantalum was dispersed in 80 ml of toluene, to which 19 g of pentaethoxytantalum that had been dissolved previously in 80 ml of toluene was added dropwise in a nitrogen gas atmosphere. The resultant solution was stirred at 60° C. for 1.5 hours, and the solvent was then removed therefrom at 55° C. by distillation. As a result, 31.1 g of dichlorotriethoxytantalum was obtained as a residue in the form of white solid.

This solid was dissolved in 80 ml of diethyl ether. The mixture was cooled to −40° C., to which 141 ml of diethyl ether solution of methyllithium (1.1 mol/l) was added dropwise, little by little. The resultant solution was stirred at −40° C. for 1.5 hours. The solvent was then removed therefrom by distillation. Light brown solid obtained as the residue was subjected to reduced pressure distillation at 40° C. and 0.7 Torr to obtain 8.5 g of a colorless transparent liquid. This liquid was analyzed in the same manner as in Example 1. The liquid had the above mentioned physical properties and was determined as trimethyldiethoxytantalum.

EXAMPLE 4

13.1 g of pentachlorotantalum was dispersed in 80 ml of toluene, to which 9.9 g of pentaethoxytantalum that had been dissolved previously in 80 ml of toluene was added dropwise in a nitrogen gas atmosphere. The resultant solution was stirred at 60° C. for 1.5 hour, and the solvent was then removed therefrom at 55° C. by distillation. As a result, 22.3 g of trichlorodiethoxytantalum [$TaCl_3(OC_2H_5)_2$] was obtained as a residue in the form of white solid.

This solid was dissolved in 80 ml of diethyl ether. The mixture was cooled to −40° C., to which 145 ml of diethyl ether solution of methyllithium (1.1 mol/l) was added dropwise, little by little. The resultant solution was stirred at −40° C. for 1.5 hours. The solvent was then removed therefrom by distillation. Brown solid obtained as the residue was subjected to reduced pressure distillation at 50° C. and 2.5 Torr to obtain 14.3 g of a colorless transparent liquid. This liquid was analyzed in the same manner as in Example 1. The liquid had the above mentioned physical properties and was determined as trimethyldiethoxytantalum.

EXAMPLE 5

20.6 g of pentaethoxytantalum was dissolved in 80 ml of diethyl ether. The mixture was cooled to −40° C. in a nitrogen gas atmosphere, to which 92 ml of diethyl ether solution of methyllithium (1.1 mol/l) was added dropwise, little by little. The resultant solution was stirred at −40° C. for 1.5 hours. The solvent was then removed therefrom by distillation. A yellow viscous liquid obtained as the residue was subjected to reduced pressure distillation at 32° C. and 0.9 Torr to obtain 5.6 g of a colorless, transparent liquid. This liquid was analyzed in the same manner as in Example 1. The liquid had the above mentioned physical properties and was determined as trimethyldiethoxytantalum.

EXAMPLE 6

A $Ta_2O_5$ film of approximately 100 Å was formed at a forming rate of approximately 30 Å/min on a silicon substrate by means of heat CVD method with trimethyldiethoxytantalum obtained in the above mentioned Example 1 under following conditions.

Source Temperature: 20° C.
Substrate Temperature: 450° C.
Carrier Gas Flow Rate ($N_2$): 20 sccm
Diluent Gas Flow Rate ($N_2$): 280 sccm
Oxygen Gas Flow Rate: 100 sccm Note: "sccm" is the abbreviation for "standard cubic centimeter per minute".

EXAMPLE 7

20.7 g of pentachlorotantalum was dispersed in 100 ml of toluene, to which 88.5 ml of isopropyl alcohol was added dropwise in a nitrogen gas atmosphere. The resultant solution was stirred at room temperature for 1.5 hours, and was then heated to 45° C. to remove the solvent therefrom by distillation. As a result, 24.8 g of dichlorotriisopropoxytantalum [$TaCl_2(OCH(CH_3)_2)_3$] was obtained as a residue in the form of white solid.

This solid was dissolved in 120 ml of diethyl ether. The mixture was cooled to −40° C., to which 140 ml of diethyl ether solution of methyllithium (1.2 mol/l) was added dropwise, little by little. The resultant solution was stirred at −40° C. for 1.5 hours. The solvent was then removed therefrom by distillation. Light brown solid obtained as the residue was subjected to reduced pressure distillation at 45° C. and 0.7 Torr to obtain 10.3 g of a colorless transparent liquid.

This liquid was analyzed through gas chromatography (column: Silicone OV-101, 25 m×0.25 mmφ), $^1$H-NMR, and $^{13}$C-NMR. As a result, it was found that this liquid is a sole substance. The liquid had the above mentioned physical properties and was determined as trimethyldiisopropoxytantalum.

EXAMPLE 8

A $Ta_2O_5$ film of approximately 100 Å was formed at a forming rate of approximately 30 Å/min on a silicon substrate by means of heat CVD method with trimethyldiisopropoxytantalum obtained in the above mentioned Example 7 under following conditions.

Source Temperature: 30° C.
Substrate Temperature: 450° C.
Carrier Gas Flow Rate ($N_2$): 20 sccm
Diluent Gas Flow Rate ($N_2$): 280 sccm
Oxygen Gas Flow Rate: 100 sccm

EXAMPLE 9

25.6 g of pentachlorotantalum was dissolved in 100 ml of toluene, to which 130 ml of sec-butyl alcohol was added dropwise in a nitrogen gas atmosphere. The resultant solution was stirred at room temperature for 1.5 hours, and was then heated to 45° C. to remove the solvent therefrom. As a result, 34.2 g of dichloro-tri-sec-butoxytantalum $TaCl_2[OCH(CH_3)C_2H_5]_3$ was obtained as a residue in the form of white solid.

This solid was dissolved in 120 ml of diethyl ether. The mixture was cooled to −40° C., to which 180 ml of diethyl ether solution of methyllithium (1.2 mol/l) was added dropwise, little by little. The resultant solution was stirred at −40° C. for 1.5 hours. The solvent was then removed therefrom by distillation. Light brown solid obtained as the residue was subjected to reduced pressure distillation at 58° C. and 0.15 Torr to obtain 13.9 g of a colorless transparent liquid.

This liquid was analyzed through gas chromatography (column: Silicone OV-101, 25 m×0.25 mmφ), $^1$H-NMR and $^{13}$C-NMR As a result it was found that this liquid is a sole substance. The liquid had the above mentioned physical properties and was determined as trimethyl-di-sec-butoxytantalum.

EXAMPLE 10

A $Ta_2O_5$ film of approximately 100 Å was formed at a forming rate of approximately 30 Å/min on a silicon substrate by means of heat CVD method with trimethyl-di-sec-butoxytantalum obtained in the above mentioned Example 9 under following conditions.

Source Temperature: 60° C.

Substrate Temperature: 450° C.
Carrier Gas Flow Rate (N$_2$): 20 sccm
Diluent Gas Flow Rate (N$_2$): 280 sccm
Oxygen Gas Flow Rate: 100 sccm The novel compounds according to the present invention have a high vapor pressure and permit effective formation of a uniform film of tantalum oxide with good properties by means of the CVD method. Such compounds are so useful for manufacturing semiconductor devices. In addition, the method according to the present invention has an effect of providing a simple and easy way of production of the above mentioned compounds with high purity.

What is claimed is:

1. A method of producing a tantalum compound represented by the following formula (1):

$$Ta(CH_3)_3(OR)_2 \qquad (1),$$

which comprises:

reacting a haloalkoxytantalum compound represented by the following formula (2):

$$TaX_2(OR)_3 \qquad (2),$$

wherein X is halogen and R is an alkyl group having from 2 to 7 carbon atoms, with a methylmetal compound; and recovering the tantalum compound represented by the formula (1) by means of reduced pressure distillation.

2. A method of forming a tantalum oxide film on a substrate by means of chemical vapor deposition with a tantalum compound represented by the following formula (1):

$$Ta(CH_3)_3(OR)_2 \qquad (1),$$

wherein R is an alkyl group having from 2 to 7 carbon atoms.

* * * * *